(12) United States Patent
Pelissier et al.

(10) Patent No.: US 12,051,195 B2
(45) Date of Patent: Jul. 30, 2024

(54) METHOD AND SYSTEM TO ASSESS MEDICAL IMAGES FOR SUITABILITY IN CLINICAL INTERPRETATION

(71) Applicant: Clarius Mobile Health Corp., Vancouver (CA)

(72) Inventors: Laurent Pelissier, North Vancouver (CA); Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 489 days.

(21) Appl. No.: 17/225,090

(22) Filed: Apr. 7, 2021

(65) Prior Publication Data
US 2022/0327691 A1    Oct. 13, 2022

(51) Int. Cl.
| | |
|---|---|
| G06K 9/00 | (2022.01) |
| G06N 3/045 | (2023.01) |
| G06N 3/08 | (2023.01) |
| G06T 7/00 | (2017.01) |
| G16H 30/20 | (2018.01) |
| G16H 30/40 | (2018.01) |
| G16H 50/20 | (2018.01) |

(52) U.S. Cl.
CPC .......... *G06T 7/0012* (2013.01); *G06N 3/045* (2023.01); *G06N 3/08* (2013.01); *G16H 30/20* (2018.01); *G16H 30/40* (2018.01); *G16H 50/20* (2018.01); *G06T 2207/20081* (2013.01); *G06T 2207/30004* (2013.01); *G06T 2207/30168* (2013.01)

(58) Field of Classification Search
None
See application file for complete search history.

(56) References Cited

U.S. PATENT DOCUMENTS

| | | | |
|---|---|---|---|
| 2017/0262982 A1 | 9/2017 | Pagoulatos et al. | |
| 2020/0049785 A1* | 2/2020 | Liu | ........................ A61B 5/055 |
| 2020/0395119 A1* | 12/2020 | Lyman | ................. G06Q 10/105 |

FOREIGN PATENT DOCUMENTS

| | | | | |
|---|---|---|---|---|
| JP | 7051849 B2 * | 4/2022 | ............... | G06N 3/04 |
| WO | WO-2022011342 A1 * | 1/2022 | ........... | A61C 9/0053 |

* cited by examiner

*Primary Examiner* — Wei Wen Yang
(74) *Attorney, Agent, or Firm* — Julian Ho; Susan Ben-Oliel

(57) ABSTRACT

A method and system for assessing medical images for suitability in clinical interpretation is described herein. The method and system involve: acquiring a medical image; inputting the medical image into a machine learning model, wherein the machine learning model is configured to determine a quality value based on the medical image; determining whether the quality value meets a quality threshold associated with a target clinical application; and when the quality value meets the quality threshold associated with the target clinical application, permitting clinical interpretation of the medical image for the target clinical application.

18 Claims, 9 Drawing Sheets

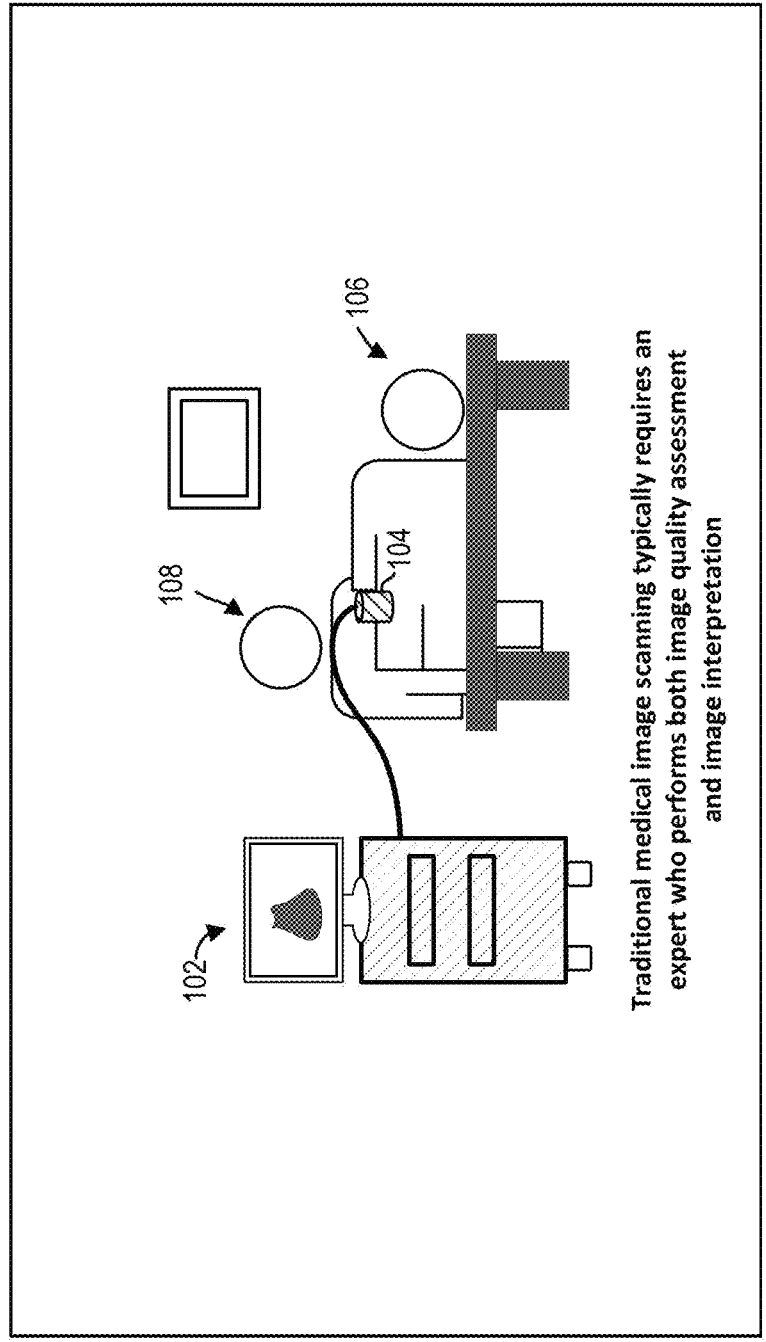

METHOD AND SYSTEM TO ASSESS MEDICAL IMAGES FOR SUITABILITY IN CLINICAL INTERPRETATION

FIELD

The described embodiments relate to assessment of medical images, and in particular, to a system and method to assess medical images for suitability in clinical interpretation.

INTRODUCTION

Medical imaging is often performed in clinical settings for diagnostic and treatment purposes. Diagnostic exams (e.g., diagnostic radiology exams), for example, may rely on medical images to screen patients for various medical ailments, including cancerous tumors as well as diseases of the heart and vascular or circulatory systems. The medical images used for patient screening may be captured using different imaging techniques including, inter alia, ultrasound imaging (e.g., sonographic images), magnetic resonance imaging (MRI), and imaging via computerized tomography (CT), mammography and/or positron emission tomography (PET).

Medical imaging procedures typically require the presence of skilled technicians to operate the medical imaging devices. Additionally, medical diagnostic experts (e.g., radiologists) may be expected to analyze captured images, and to assess whether the images are of sufficient quality for diagnostic interpretation.

Ultrasound imaging systems, in particular, are becoming increasingly accessible. Some modern ultrasound medical imaging systems connect to off-the-shelf display computing devices such as those running iOS™ or Android™ operating systems. However, because traditional usage patterns require the presence of a skilled technician and/or a medical diagnostic expert to acquire images, it is difficult for inexperienced users to acquire images that are of a sufficient quality for clinical interpretation.

There is thus a need for improved systems and methods to assess medical images for suitability in clinical interpretation. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein. The foregoing is not an admission that anything discussed below is part of the prior art or part of the common general knowledge of a person skilled in the art.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 1 is a schematic illustration of a conventional process for medical imaging.

Figure 2A:
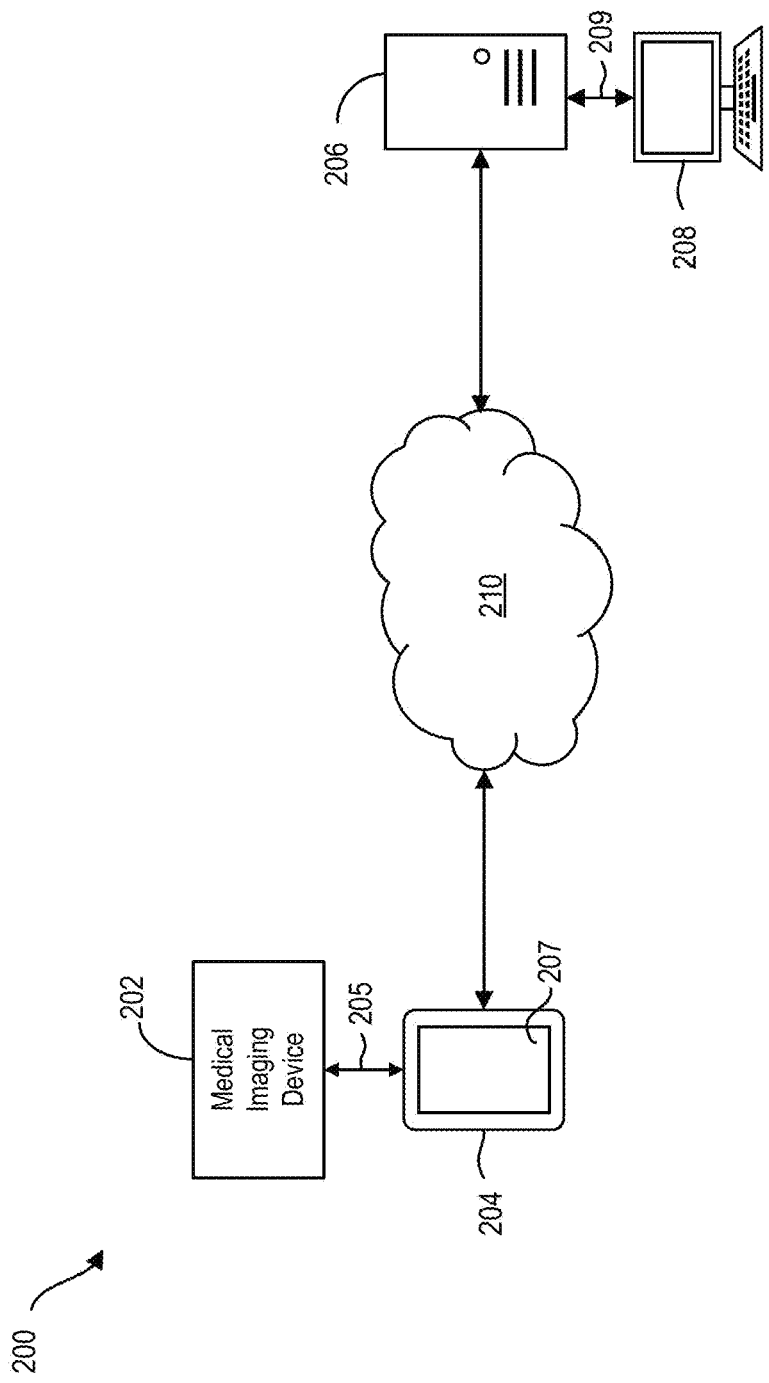
FIG. 2A is a system to assess medical images for suitability in clinical interpretation, according to some embodiments of the present invention.

Further aspects and features of the example embodiments described herein will appear from the following description taken together with the accompanying drawings.

DETAILED DESCRIPTION OF THE EMBODIMENTS

In a first broad aspect of the present disclosure, there is provided a method for assessing medical images for suitability in clinical interpretation, the method including: acquiring a medical image; inputting the medical image into a machine learning model, wherein the machine learning model is configured to determine a quality value based on the medical image; determining whether the quality value meets a quality threshold associated with a target clinical application; and when the quality value meets the quality threshold associated with the target clinical application, permitting clinical interpretation of the medical image for the target clinical application.

In some embodiments, when it is determined that the medical image meets the threshold associated with the target clinical application, the method further includes: analyzing the medical image to detect an image feature associated with the target clinical application. In some embodiments, the method is performed on a computing device, and prior to the analyzing, the method further includes: transmitting, from the computing device to a server, the medical image and the quality value of the machine learning model; storing the medical image and the quality value on the server; and retrieving, at the server, the medical image.

In some embodiments, the machine learning model is a first machine learning model, and the analyzing the medical image includes: inputting the medical image into a second machine learning model, wherein the second machine learning model is configured to detect the image feature associated with the target clinical application, for medical images that meet the quality threshold associated with the target clinical application.

In some embodiments, when training the second machine learning model, the method further includes: accessing a set of training medical images; labelling, for each of the set of training medical images, an image feature associated with the target clinical application; and training the second machine learning model to identify the image feature on future medical images.

In some embodiments, to determine the quality threshold associated with the target clinical application, the method further includes: determining image quality values of the medical images in the set of training medical images; and setting the quality threshold associated with the target clinical application to correspond to the image quality values of the medical images in the set of training medical images used to train the second machine learning model.

In some embodiments, the method further includes: determining whether the quality value meets another quality threshold associated with another target clinical application; and when the quality value meets the another quality threshold associated with the another target clinical application, permitting clinical interpretation of the medical image for the another target clinical application.

In some embodiments, the target clinical application comprises identifying kidney stones, and the another target clinical application comprises identifying gallstones, and wherein the quality threshold associated with the target clinical application is higher than the quality threshold associated with the another target clinical application.

In some embodiments, the target clinical application comprises identifying a ventricle, and the another target clinical application comprises identifying pericardial effusion, and wherein the quality threshold associated with the target clinical application is higher than the quality threshold associated with the another target clinical application.

In some embodiments, when training the machine learning model, the method further includes: accessing a set of training medical images; labeling each of the set of training medical images with an image quality value; and training the machine learning model using the set of labeled training medical images to predict image quality values for new medical images.

In another broad aspect of the present disclosure, there is provided a system for assessing medical images for suitability in clinical interpretation, the system including: a computing device comprising one or more device processors and a device memory storing device instructions for execution by the one or more device processors, wherein when the device instructions are executed by the one or more device processors, the one or more device processors are configured to: acquire a medical image; and input the medical image into a machine learning model, wherein the machine learning model is configured to determine a quality value based on the medical image; and a server comprising one or more server processors and a server memory storing server instructions for execution by the one or more server processors, wherein when the server instructions are executed by the one or more server processors, the one or more server processors are configured to: determine whether the quality value meets a quality threshold associated with a target clinical application; and when the quality value meets the quality threshold associated with the target clinical application, permit clinical interpretation of the medical image for the target clinical application.

In some embodiments, when it is determined that the medical image meets the threshold associated with the target clinical application, the server is further configured to: analyze the medical image to detect an image feature associated with the target clinical application.

In some embodiments, prior to the analyzing, the computing device is further configured to: transmit, to a server, the medical image and the quality value of the machine learning model; and the server is further configured to: store the medical image and the quality value; and retrieve the medical image.

In some embodiments, the machine learning model is a first machine learning model, and the analyzing the medical image comprises: inputting the medical image into a second machine learning model, wherein the second machine learning model is configured to detect the image feature associated with the target clinical application, for medical images that meet the quality threshold associated with the target clinical application.

In some embodiments, when training the second machine learning model, the server is further configured to: access a set of training medical images; receive inputs that label, for each of the set of training medical images, an image feature associated with the target clinical application; and train the second machine learning model to identify the image feature on future medical images.

In some embodiments, to determine the quality threshold associated with the target clinical application, the server is further configured to: determine image quality values of the medical images in the set of training medical images; and set the quality threshold associated with the target clinical application to correspond to the image quality values of the medical images in the set of training medical images used to train the second machine learning model.

In some embodiments, the server is further configured to: determine whether the quality value meets another quality threshold associated with another target clinical application; and when the quality value meets the another quality threshold associated with the another target clinical application, permit clinical interpretation of the medical image for the another target clinical application.

In some embodiments, the target clinical application comprises identifying kidney stones, and the another target clinical application comprises identifying gallstones, and wherein the quality threshold associated with the target clinical application is higher than the quality threshold associated with the another target clinical application.

In some embodiments the target clinical application comprises identifying a ventricle, and the another target clinical application comprises identifying pericardial effusion, and wherein the quality threshold associated with the target clinical application is higher than the quality threshold associated with the another target clinical application.

In some embodiments, when training the machine learning model, the server is further configured to: access a set of training medical images; receive inputs that label each of the set of training medical images with an image quality value; and train the machine learning model using the set of labeled training medical images to predict image quality values for new medical images.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures, and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a schematic illustration of an example conventional process for medical imaging. As shown, a medical imaging device 102 (e.g., an ultrasound machine connected to a transducer probe 104) is provided for capturing medical images of a patient 106. A skilled imaging device technician 108 (e.g., an ultrasound technician) or medical professional (e.g., specialist physician or veterinarian) is typically in attendance to operate the imaging device 102 with a view to capturing images of the patient 106. The operator of the imaging device 102 is typically performing both image quality assessment (e.g., determine whether an acquired image is of a suitable image quality for interpretation), as well as image interpretation itself (e.g., interpret the image to determine a medical condition in the imaged tissue).

In this conventional process for medical imaging, the patient imaging scanning process is highly coupled to the image interpretation process. In other words, image scanning often cannot occur independently from image interpretation. This, in turn, creates a bottleneck whereby the availability of the image scanning procedure is limited by the availability of a skilled technician or other medical professional to be present and available for image acquisition and interpretation. This bottleneck has limited the widespread adoption and associated medical benefits of portable imaging devices which can capture images outside of clinical settings.

In view of the foregoing, methods and systems provided herein allow assessing medical images for suitability in clinical interpretation. In some embodiments, the system and method herein can be considered as providing real-time scanning quality control of medical images. In particular, the provided methods and systems allow for assessing—in real-time, or near real-time—the quality of images captured by medical imaging devices. The present systems may remove the bottleneck of a skilled technician or medical professional being attendant during the image scanning process to ensure quality control during image capture. In this manner, the image quality assessment can be decoupled from the image interpretation. In turn, this may allow more patients have their medical images acquired with the medical images being of a suitable quality for later clinical interpretation.

Referring to FIG. 2A, there is shown a block diagram of an example system 200 to assess medical images for suitability in clinical interpretation.

As shown, the system 200 generally includes a medical imaging device 202 and a computing device 204, which are connected via network 210 to a server 206. In some embodiments, the system 200 may also include a remote computer terminal 208 in communication with the server 206.

Medical imaging device 202 may be any device configurable to capture medical images of patients. For example, the medical imaging device 202 may be an ultrasound imaging apparatus for capturing ultrasound images (e.g., sonograms). In particular, the imaging device 202 can include a probe (or transducer) which emits ultrasound waves, and detects reflected waves to form an image. In other example embodiments, the imaging device 202 may be, for example, a magnetic resonance imaging (MRI) device, a computed tomography (CT) imaging device, as well as various devices based on mammography, positron emission tomography (PET), or other suitable imaging techniques. In various cases, the medical imaging device 202 may be a portable device (e.g., a handheld device) that provides convenient, on-demand medical imaging inside or outside of clinical settings.

While not shown, the medical imaging device 202 may include one or more of a memory for storing received imaging data (e.g., ultrasound data), a processor to process received data, and a communication interface to allow the medical imaging device 202 to transmit the imaging data to external devices such as computing device 204. For example, in cases where the medical imaging device 202 is a handheld ultrasound scanner, the processor may contain analog-to-digital (ADC) converters and/or integrated circuits programmed to scan convert ultrasound image data. In some cases, the communication interface may be configured to communicate data using wireless communication protocols, including WiFi™ or Bluetooth™. In other cases, data can be communicated via a wired connection.

Computing device 204 may be any suitable computer capable of executing one or more application programs. Computing device 204 can include desktop computers, but in some embodiments, may be mobile devices such as smartphones, tablets or laptops, wearable computing devices such as smartwatches, smart glasses and/or generally any smart devices that may be networked (e.g., through the "Internet of Things"). In some cases, computing device 204 can also include digital media receivers, as well medical diagnostic equipment.

In various embodiments, as illustrated in FIG. 2A, the computing device 204 may be directly coupled to the medical imaging device 202. For example, computing device 204 may be in close proximity to the imaging device 202, and may be in direct communication, via a communication link 205 to receive captured medical imaging data (e.g., ultrasound data). The communication link 205 may be a wired or wireless communication link. In cases where the communication link 205 is a wireless link, the link may rely on any suitable wireless communication protocol including, by way of non-limiting examples, WiFi™ or Bluetooth™, or other suitable two-way radio communications protocols. In some cases, the wireless link 205 may occur via the network 210.

In at least some embodiments, the computing device 204 may receive captured medical image data in real-time, or near real-time, from the imaging device 202. In example embodiments where the medical imaging device 202 is an ultrasound imaging scanner, scan conversion may be performed either by the ultrasound scanner 202 and/or by the computing device 204. For example, in some embodiments, pre-scan converted data ultrasound image data may be sent by an ultrasound scanner 202 to a computing device 204, and scan conversion may be performed at the computing device 204 prior to display of the ultrasound image data thereon. In various embodiments, the machine learning models described herein may be trained on, and configured to take as input, pre-scan converted ultrasound image data, as is described in Applicant's Co-pending U.S. patent application Ser. No. 17/187,851 entitled "Method and System for Training and Deploying Artificial Intelligence Model on Pre-Scan Converted Ultrasound Image Data", the entire contents of which are hereby incorporated by reference.

Referring still to FIG. 2A, the received medical images can be displayed to a user of the computing device 204 on a display screen 207. In this manner, a user may be able to review images captured by the imaging device 202. In some embodiments, the computing device 204 may also be configurable to transmit data to the imaging device 202, including transmitting various instruction or commands (e.g., commands to vary an image capture setting of the imaging device 202, etc.).

As explained in further detail herein, in various embodiments, the computing device 204 may store and execute an image quality (IQ) assessment program (also called an IQ program herein). The IQ assessment program may be configurable to determine, in real-time or near real-time, the quality of images captured and received from the medical imaging device 202.

Server 206 may be a computer server that is connected to network 210. As with all devices shown in the system 200, there may be multiple servers 206, although not all are shown. It will also be understood that the server 206 need not be a dedicated physical computer. For example, the various logical components that are shown as being provided on server 206 may be hosted by a third party "cloud" hosting service such as Amazon™ Web Services™ Elastic Compute Cloud (Amazon EC2).

As provided in further detail herein, the server 206 may include a data storage component for storing data for subsequent retrieval. For instance, the data storage component may receive and store images previously captured by the medical imaging device 202, and which are transmitted by the computing device 204 (e.g., via network 210). In various embodiments provided herein, the server 206 may also store and execute an image interpretation program which can be used to analyze received medical images to identify one or more target image features.

In some embodiments, system 200 can also include a remote computing terminal 208, which similar to computing device 204, may comprise any suitable computing device. The remote terminal 208 may communicate with the server 206 via communication link 209, which can be a wired or wireless link. In at least some example embodiments, the remote terminal 208 may be a computer associated with a medical diagnostic expert. In particular, the medical diagnostic expert may use the remote terminal 208, for example, to review and analyze images previously captured by the medical imaging device 202 in order to provide a diagnostic assessment.

Network 210 may use one or more computer network technologies, such as IEEE 802.3 (Ethernet), IEEE 802.11 and the like. In various embodiments, network 210 may include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A network could also mean dedicated connections between computing devices and electronic components, such as buses for intra-chip communications.

In some cases, network 210 may be connected to the Internet. Typically, the connection between network 210 and the Internet may be made via a firewall server (not shown). In some cases, there may be multiple links or firewalls, or both, between network 210 and the Internet. Some organizations may operate multiple networks 210 or virtual networks 210, which can be internetworked or isolated. These have been omitted for ease of illustration, however it will be understood that the teachings herein can be applied to such systems.

Figure 2C:
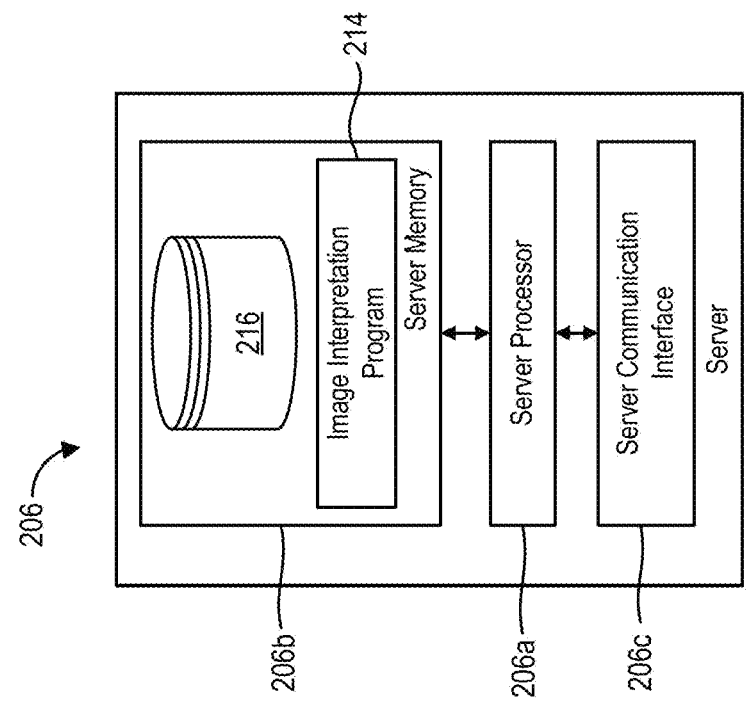
FIG. 2C is a simplified block diagram for an example server, according to some embodiments of the present invention.
Figure 2B:
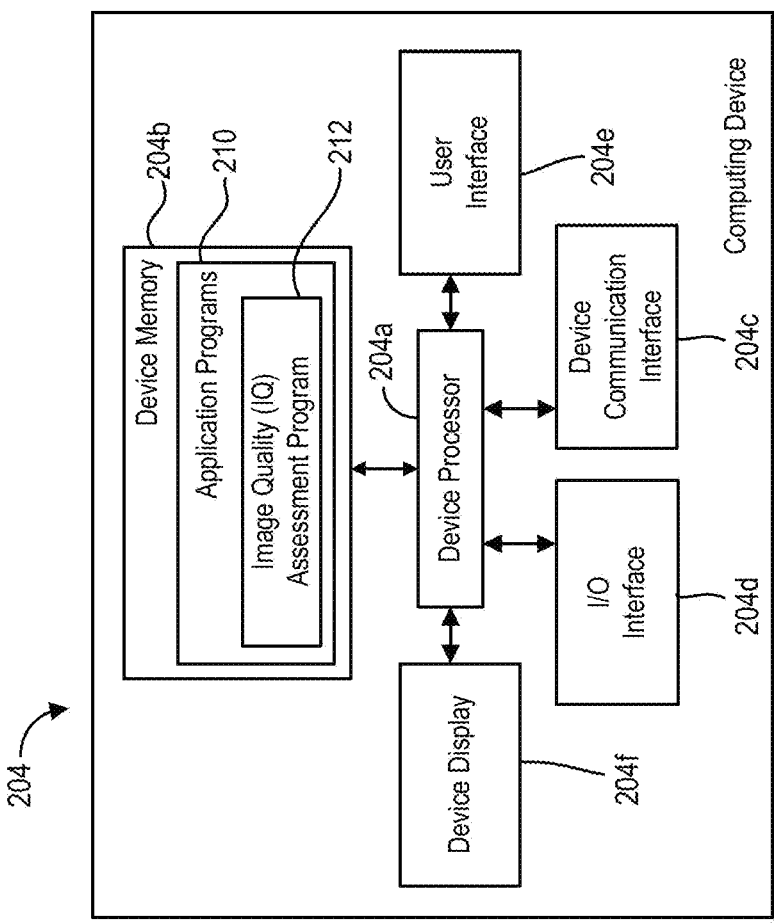
FIG. 2B is a simplified block diagram for an example computing device, according to some embodiments of the present invention.

Referring now to FIG. 2B, there is shown a simplified hardware/software block diagram for the example computing device 204 illustrated in FIG. 2A, in accordance with some example embodiments.

As shown, computing device 204 may include a device processor 204a coupled, via a computer data bus, to one or more of a device memory 204b and a device communication interface 204c. In some cases, the device processor 204a may be also coupled to an input/output (I/O) interface 204d, a user interface 204e and/or a device display 204f.

Device processor 204a may be a computer processor, such as a general purpose microprocessor. In some other cases, processor 204a may be a field programmable gate array (FPGA), application specific integrated circuit (ASIC), microcontroller, or other suitable computer processor. In some embodiments, the processor 204a may include hardware elements that are particularly suitable for machine learning activities such as graphics cards.

Device processor 204a may be coupled, via the computer data bus, to device memory 204b. Device memory 204b may include both volatile and non-volatile memory. Non-volatile memory may store computer programs consisting of computer-executable instructions, which may be loaded into the volatile memory for execution by processor 204a as needed. It will be understood that references herein to computing device 204 as carrying out a function or acting in a particular way imply that processor 204a is executing instructions (e.g., a software program) stored in memory 204b and possibly transmitting or receiving inputs and outputs via one or more interfaces. Memory 204b may also store data input to, or output from, processor 204a in the course of executing the computer-executable instructions.

As shown, device memory 204b can store one or more application programs 210, including a medical IQ assessment program 212. As provided herein, the image quality IQ program 212 is configured to receive input medical images from medical imaging device 202 (as shown in FIG. 2A). For example, the images may be received in real-time, or near real-time, from medical imaging device 202. The received images may then be further analyzed by the IQ program 212 to determine whether the images are suitable for clinical interpretation (e.g., whether an image is of a sufficient quality for diagnostic assessment). Where an image is determined not to be suitable for clinical interpretation, the IQ program 212 may—for example—prompt the user to re-apply the imaging device 202 to capture a new image.

It has been appreciated that an assessment of the quality of a medical image is often contingent on the clinical application for which the image is being captured for. For example, some clinical applications may require higher quality image captures than other clinical applications. For instance, diagnosing kidney stones in abdominal imaging can often demand near perfect image quality acquisition owing to the granular detail required to effectively assess kidney stone condition. In contrast, gallstones in the gallbladder are more easily observable (e.g., identifiable) in images because of the recognizable bright structures (stones) with black shadows, and accordingly, can be evaluated using lesser quality images. Similarity, calculation of ejection fraction (EF) based on cardiac images can demand higher quality images as compared to assessments of pericardial effusion (i.e., "fluid around the heart"), as EF requires clear delineation of cardiac structures (e.g., a ventricle), while pericardial effusion only looks at large black (fluid) areas.

As provided herein, the IQ program 212 may be able to generate determinations of image quality. For example, the IQ program 212 may be able to take an image as input and output a quality value (e.g., a percentage between 0%-100%, where a 100% rating may indicate perfect quality and a 0% rating may indicate very low/poor image quality).

As discussed below, the quality value may be considered a universal or otherwise objective measurement of image quality, regardless of the clinical application in which the image is intended to be used. In these embodiments, different target applications may have different quality thresholds to determine suitability using this objective measure. For example, in some embodiments, the IQ program 212 may use a determined quality value and compare it to a quality threshold necessary for a given target clinical application. The output of this determination may be a binary output that indicates whether an input image is suitable (e.g., meets the threshold) or not suitable (e.g., does not meet the threshold) for the specific clinical application.

In various embodiments, the IQ program 212 may generate a quality value for a medical image by processing it through a neural network that uses a trained machine learning model to provide the quality value (e.g., 0-100%). In various embodiments, the neural network may take as input a processed image (e.g., grading it for quality with regards to clarity, resolution, and/or contrast) and/or a histogram of the image (e.g., grading it for quality with respect to speckle size). In some embodiments, a combination of these approaches may be used.

Additionally or alternatively, in some embodiments, the IQ program 212 may be able to generate application-specific determinations of image quality (e.g., one that is not objective or universal in nature). For example, the IQ program 212 may be configured to determine whether an image is of sufficient quality for a particular target clinical application (e.g., diagnosing kidney stones). In these embodiments, the particular application-specific image quality values can be used for determining whether given images are suitable for clinical interpretation in that particular clinical application.

By providing scanning quality control for medical images at the point of image capture, the IQ program 212 may decouple the medical image scanning process from the image interpretation process. More specifically, the IQ program 212 may address challenges in conventional image scanning procedures whereby skilled personnel (e.g., a skilled technician 110 in FIG. 1) are required to be attendant to acquire and review images in real-time in order to assess whether captured images are suitable for clinical interpretation. Rather, the IQ assessment program 212 provides the automated feedback regarding whether captured images are of sufficient quality. In turn, the clinical interpretation may be conducted independently, and subsequently at a later point in time. For example, using the remote computer terminal 208, a diagnostic expert may, at a future point in time, clinically interpret the images (e.g., for diagnostic assessment).

Referring still to FIG. 2B, computing device 204 may also include a device communication interface 204c. Communication interface 204c may be one or more data network interfaces, such as an IEEE 802.3 or IEEE 802.11 interface, for communication over a network. In various cases, communication interface 204c can be used to receive, in real-time or near real-time, medical images captured by the medical image device 202.

Additionally or alternatively, communication interface 204c can allow programs 210 to transmit to, or retrieve data from, server 206. For example, computing device 204 may transmit, via communication interface 204c, medical images captured by the imaging device 202 to server 206 for storage on the server 206. In other cases, and as explained in greater detail herein, computing device 204 may also transmit the output of the image quality assessment program 212 to the server 206.

Input/Output (I/O) interface 204d may be provided to allow for coupling of other devices to the computing device 204. For example, in some cases, medical imaging device 202 can be coupled, via the I/O interface 204d, to the computing device 204. In an example embodiment, the computing device 204 can be a tablet computer, or a smartphone device that is directly couplable to a portable medical imaging device 202 such as an ultrasound scanner via the I/O interface 204d (e.g., via a USB or USB-C interface).

Display 204f may be any suitable display for outputting information and data as needed by various computer programs. For example, display 204f may be a screen integrated into the computing device 204, or in communication with the computing device 204. In some cases, display 204f may display a graphical user interface (GUI) associated with one or more applications 210. In some embodiments, display 204f may be configured as a touch-screen display. For example, display 204f may be a resistive or capacitive touchscreen which is configured to detect touch force applied by a user. In these cases, the display 204f can receive various user inputs. As provided herein, in various embodiments, the display 204f can be used to display images captured by the medical imaging device 202. Additionally or alternatively, the display 204f may also be used to display outputs of programs 210 operating on the computing device 204. For example, the display 204f may display the output of the image quality assessment program 212 to a user of the device 204.

User interface 204e may include one or more components that allow a user, or operator, to interact with the computing device 204. For example, the user interface 204e can be a keyboard or other input device that allows a user to input instructions into the computing device 204.

It will be appreciated that in various embodiments, the remote terminal 208 in FIG. 2A may have a similar (or identical) hardware architecture as shown herein for the computing device 204.

Referring now to FIG. 2C, there is shown a simplified hardware/software block diagram of an example server 206, in accordance with some embodiments.

As shown, server 206 may generally include one or more of a server processor 206a in communication with a server memory 206b and/or a server communication interface 206c.

Similar to device processor 204a, server processor 206a may also be computer processor, such as a general purpose microprocessor. In some other cases, processor 204a may be a field programmable gate array (FPGA), application specific integrated circuit (ASIC), microcontroller, or other suitable computer processor. Similar to processor 204a, the processor 206a may include hardware elements that are particularly suitable for machine learning activities such as graphics cards.

The server memory 206b may also include both volatile and non-volatile memory. In various embodiments provided herein, the server memory 206b may include a database storage component 216. For example, the database storage 216 may store (e.g., archive) medical images previously captured by medical imaging device 202, and transmitted to the server 206 by computing device 204. In other cases, database storage 216 may also receive and store quality value outputs from the image quality assessment application 212, e.g., as transmitted from the computing device 204. For example, in some cases, storage 216 can store previously captured medical images, along with a corresponding quality value and/or indication of the image's clinical suitability as determined by the image quality assessment application 212.

Server memory 206b may also store an image interpretation program 214. For example, the image interpretation program 214 can be used to analyze a previously captured images (e.g., image stored on storage 216) and its associated quality value (as outputted by the IQ program 212 on computing device 204), to interpret the image for a given clinical application (e.g., kidney stones, tumors, gallstones, etc.). As discussed below, part of the analysis may include determining whether the quality value exceeds a threshold necessary to analyze the medical image for a target feature. In various embodiments, the interpretation program 214 may analyze the image to identify the presence, absence, or a changing progression (e.g., change over time) of a target image feature. In this manner, the image interpretation program 214 can provide for automated interpretation (e.g., diagnostic assessment) of captured medical images. Because the images have been previously assessed for suitability for clinical interpretation and only images that satisfy the quality threshold are used for interpretation, the output of the interpretation program 214 is more likely to increase the accuracy of the clinical assessment of the medical image.

Figure 3:
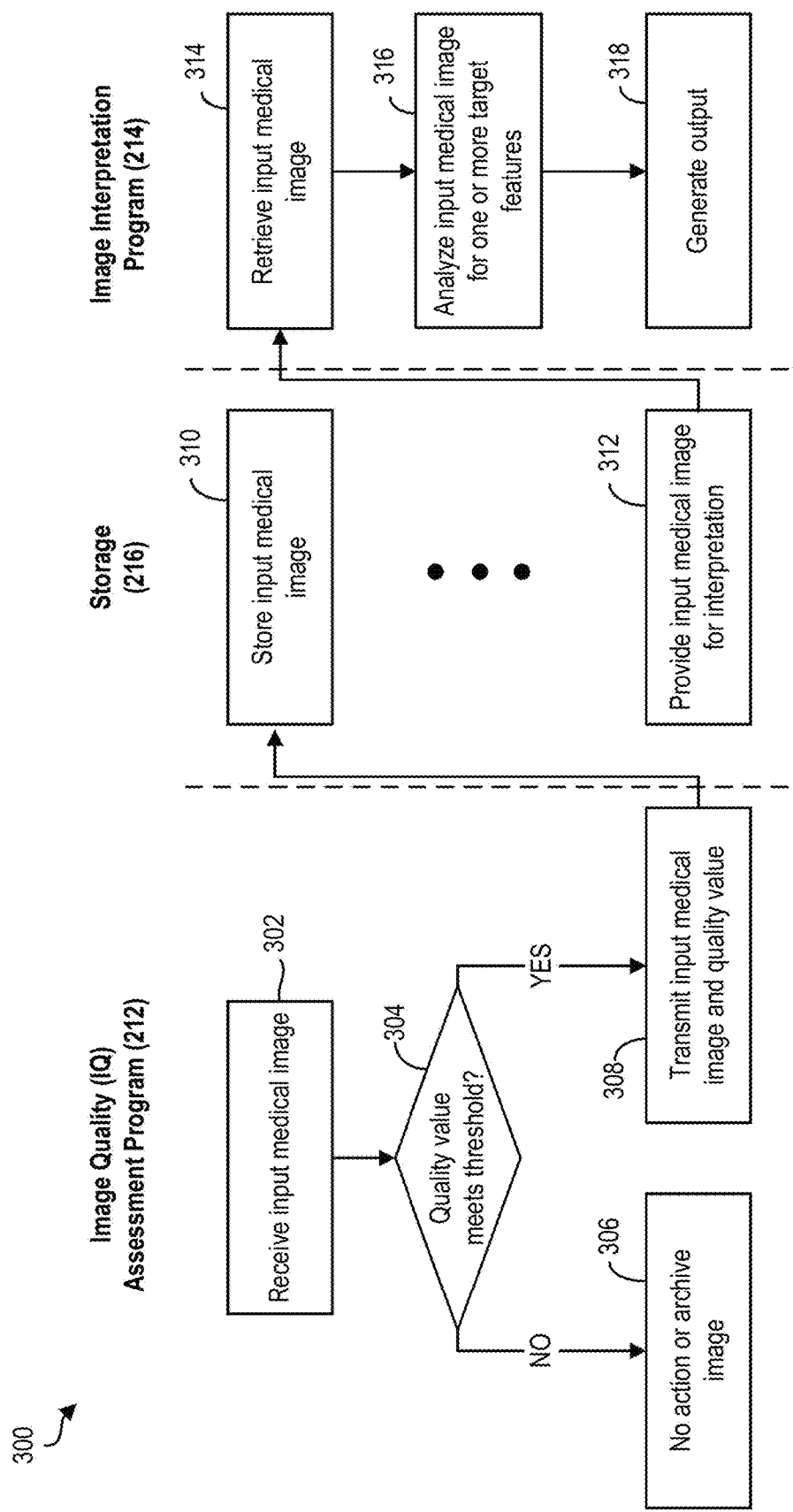
FIG. 3 is an example process flow for a method to assess medical images for suitability in clinical interpretation, according to some embodiments of the present invention.

Referring to FIG. 3, there is shown an example process flow for a method 300 for assessing medical images for suitability in clinical interpretation, according to some embodiments. Method 300 may be performed, for example, by a combination of the device processor 204a executing the IQ assessment program 212 (as shown in FIG. 2B), and the server processor 206a executing the image interpretation program 214 (as shown in FIG. 2C). In some cases, the image interpretation program 214 may also be executed by a processor of the remote computing terminal 208.

As shown, at 302, an input medical image may be received by the IQ program 212. For example, the medical image may be received in real-time, or near real-time, from the medical imaging device 202 after capturing an image of a patient. As noted, In some embodiments, the medical imaging device 202 may be an ultrasound scanner, and the medical image may be an ultrasound image acquired by the ultrasound scanner and transmitted to the computing device 204.

At 304, the IQ assessment program 212 may analyze the input medical image to determine whether the image is clinically suitable for a given target clinical application. For example, this may involve inputting the input medical image into a trained machine learning model (also called an AI model herein) that outputs a quality value or score for the medical image. As noted above, the quality value may be provided as a percentage rating (e.g. 0%-100%). Additionally or alternatively, in some cases, the quality value can be a graded rating (e.g., poor, average, excellent). Additionally or alternatively, the output assessment rating can be a numeric rating (e.g., a 1-5 rating, wherein "1" is poor image quality, and "5" is high image quality). As discussed herein, in some embodiments, the quality value may be an objective measure of image quality regardless of the intended target clinical application.

A trained machine learning model may make the determination of quality value by extracting a number of image features without being expressly programmed to. For example, the trained machine learning model may extract image features such as the image brightness, sound to noise ratio (SNR), and/or a speckle measurement, and these various features may be used by the machine learning model that mathematically weighs these different features to produce a quality value. Details of how the machine learning model can be trained are discussed further below with respect to FIG. 8.

The quality score for an inputted medical image may then be compared to a quality threshold for a given target clinical application. There may be different quality thresholds for different clinical applications. As noted above, for example, a higher quality image may be needed to effectively assess kidney stones. In contrast, a lower quality image may be sufficient for assessing gallstones in the gallbladder. Thus, the IQ assessment program may receive as input a desired clinical (e.g., assessing kidney stones or assessing gallstones), and based on the received input, make the determination at act 304 according to the threshold for inputted clinical application.

In some embodiments, the output of the machine learning model (e.g., the quality value) and/or a binary output of whether the quality value meets the quality threshold for a given clinical application can be displayed to the user of computing device 204 on display interface 204f. In various embodiments, this output can be displayed in real-time or near real-time. In cases where the quality value of the image is determined not to meet the quality threshold for a desired clinical application, the IQ program 212 may also display a prompt to the user of computing device 204 to capture a new image using the medical imaging device 202.

Referring back to FIG. 3, if the image is determined not to meet the quality threshold for a selected clinical application, then at 306, no action may be taken (e.g., the image may be disposed). In other cases, the image may be stored or archived. For example, the image may be stored on device memory 204b (as shown in FIG. 2B), or otherwise transmitted for storage on data storage component 216 of server 206 (as shown in FIG. 2C). In particular, while the image may not have a quality value that satisfies the threshold for one clinical application, the image may still be of a quality value that is sufficient for another clinical application. Accordingly, in storing the image, the image can be subsequently retrieved—at a later point in time—and re-assessed in view of a different clinical application.

Otherwise, at 308, if it is determined that the quality value of the input image meets the quality threshold, then the input image and/or its associated quality value can be transmitted to the server 206 via network 210. In some embodiments, the target clinical application of the quality threshold may also be transmitted to the server 206. Additionally or alternatively, the binary output of whether the quality threshold is met may also be transmitted to the server 206. The transmitted data may then be stored on the server storage component 216 at act 310.

Referring still to FIG. 3, after some time has passed (as shown by the vertical ellipses), the medical image stored at act 310 can be retrieved from the server storage 216 for review and clinical interpretation. At act 314, the image interpretation program 214 may retrieve the input image for analysis and act 312, the data storage component 216t may provide the input medical image for interpretation in response.

At act 316, the image interpretation program 214 may analyze the retrieved input image to identify one or more features in association with the target clinical application. The process of analyzing images by the image interpretation program 214 is explained in further detail below with reference to FIG. 5. Based on the analysis, at act 318, the image interpretation program 214 may generate an output. For example, the output can comprise a medical image that is annotated with one or more target image features.

The embodiment of FIG. 3 generally describes an example flow where the stored medical image that has been determined to meet the quality threshold is provided to the image interpretation program 214 for automated image interpretation. However, in some embodiments, the stored medical image may additionally or alternatively be provided to a human interpreter (e.g., a diagnostician operating remote terminal 208 as shown in FIG. 2) for interpretation.

As noted, by using a machine learning model to assess image quality prior to storing images, the present embodiments help ensure that only images that meet a quality threshold will be stored. In turn, this allows interpretation of the image to happen at a later time so that the process of image acquisition and the process of image interpretation can be decoupled. In this manner, the real-time or near real-time image scanning quality control provided by the IQ program 212 permits more individuals (e.g., including patients themselves) to acquire images. This may be helpful, for example, to assist patients monitor certain conditions over time (e.g., the growth of a tumor).

Figure 4:
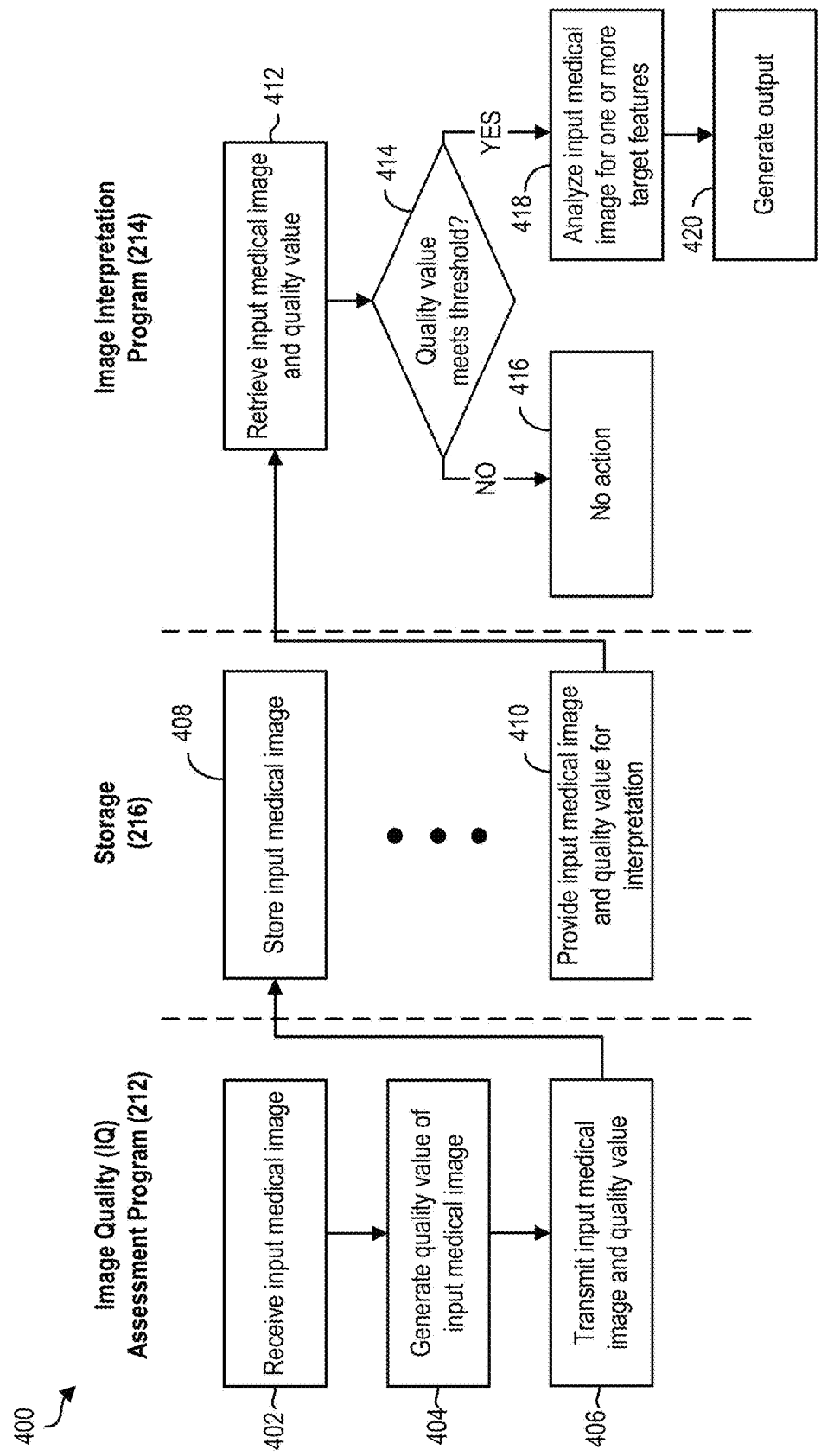
FIG. 4 is an example process flow for a method to assess medical images for suitability in clinical interpretation, according to some other embodiments of the present invention.

Referring now to FIG. 4, there is shown an example process flow for a method 400 for assessing medical images for suitability in clinical interpretation, in accordance with another embodiment. In some embodiments, method 400 may be performed by a combination of the device processor 204a executing the IQ assessment program 212 (as shown in FIG. 2B), and the server processor 206a executing the image interpretation application 214 (as shown in FIG. 2C). In other cases, the image interpretation application 214 may be executed by a processor of, for example, remote terminal 208 (as shown in FIG. 2A).

The method of FIG. 4 is similar to the method 300 of FIG. 3. However, in the method of FIG. 4, the determination of whether a quality value of an input medical image meets a threshold for a given target clinical application is not performed by the IQ assessment program 212. Rather, the quality value is stored, and only when the image is being interpreted for the target clinical application (e.g., by the image interpretation program 214), is the quality value evaluated to determine whether it meets the quality threshold for the clinical application.

At 402, an input medical image may be received by the IQ program 212. For example, the medical image may be received in real-time, or near real-time, from the medical imaging device 202, which is capturing images of a patient. This act is analogous to act 302 in FIG. 3.

At 404, the IQ assessment program 212 may analyze the input medical image to generate a quality value for the inputted medical image. For example, as was discussed above with respect to FIG. 3, this may involve inputting the input medical image into a trained machine learning model that outputs a quality value or quality score for the medical image (e.g., a quality value from 0%-100%). As noted above, in some embodiments, the quality value of the input medical image may be considered universal or objective, and independent of any intended target clinical applications.

At 406, the inputted medical image and associated quality value generated by the IQ program 212 may be transmitted to the server 206, via network 210. In some embodiments, a target clinical application that may have been inputted at the computing device 204 executing the IQ program 212 may also be transmitted to the server 206. At 408, the input medical image and associated quality value may then be stored, for example, on the server 206 data storage component 216.

At a subsequent point in time (as shown by the vertical ellipses), the medical image stored at act 408 can be retrieved from the server storage 216 for review and clinical interpretation. At act 412, the image interpretation program 214 may retrieve the input medical image and associated quality value. In response, at 410, the storage component 216 may provide these items to the image interpretation program 214. If stored at the storage component 216, the image interpretation program 214 may also retrieve a target clinical application.

At 414, the interpretation program 214 may determine whether the quality value meets a threshold. Depending on how the quality value is stored (e.g., as a score from 0-100% or at a higher level categorization of "poor", "average", or "excellent"), this may be performed in different ways. For example, the interpretation program 214 can determine whether the assessment rating is above an "average" classification, and/or if the quality value rating is above a minimum percentage quality value (e.g., 50%).

As noted, in at least some embodiments, the quality value threshold may be different for different target clinical applications (e.g., feature identification and/or diagnostic interpretation). For example, the quality value threshold may be higher for clinical applications that require identifying smaller features (e.g., kidney stones), and lower for clinical applications that only require identifying relatively larger features (e.g., gallstones in the gallbladder). Accordingly, the image interpretation program 214 may store a look-up table and/or database of clinical applications and corresponding quality value thresholds. In various cases, image interpretation program 214 can receive input that indicates the relevant clinical application—for the purpose of accessing the look-up table—either directly from a user input, or from the IQ program (if received there and transmitted for storage on storage component 216). Based on this input, the appropriate quality threshold may be used during act 414.

At 416, if the quality value is below the threshold, then the interpretation program 214 may take no action with respect to the input image. In some embodiments, the interpretation program 214 may generate an output (e.g., a notification) to a user (e.g., a user of remote terminal 208) that the available input image is not suitable for interpretation in the target clinical application.

Otherwise, at 418, if the quality value is above the quality threshold, then the image can be determined to be suitable for interpretation in the target clinical application. As discussed further below, the image interpretation program 214 may then analyze the image to identify one or more target features in association with the target clinical application.

At 420, based on the analysis, the image interpretation program 214 may generate an output. For example, the output can correspond to a version of the input medical image that has been annotated with the target image features.

Figure 5:
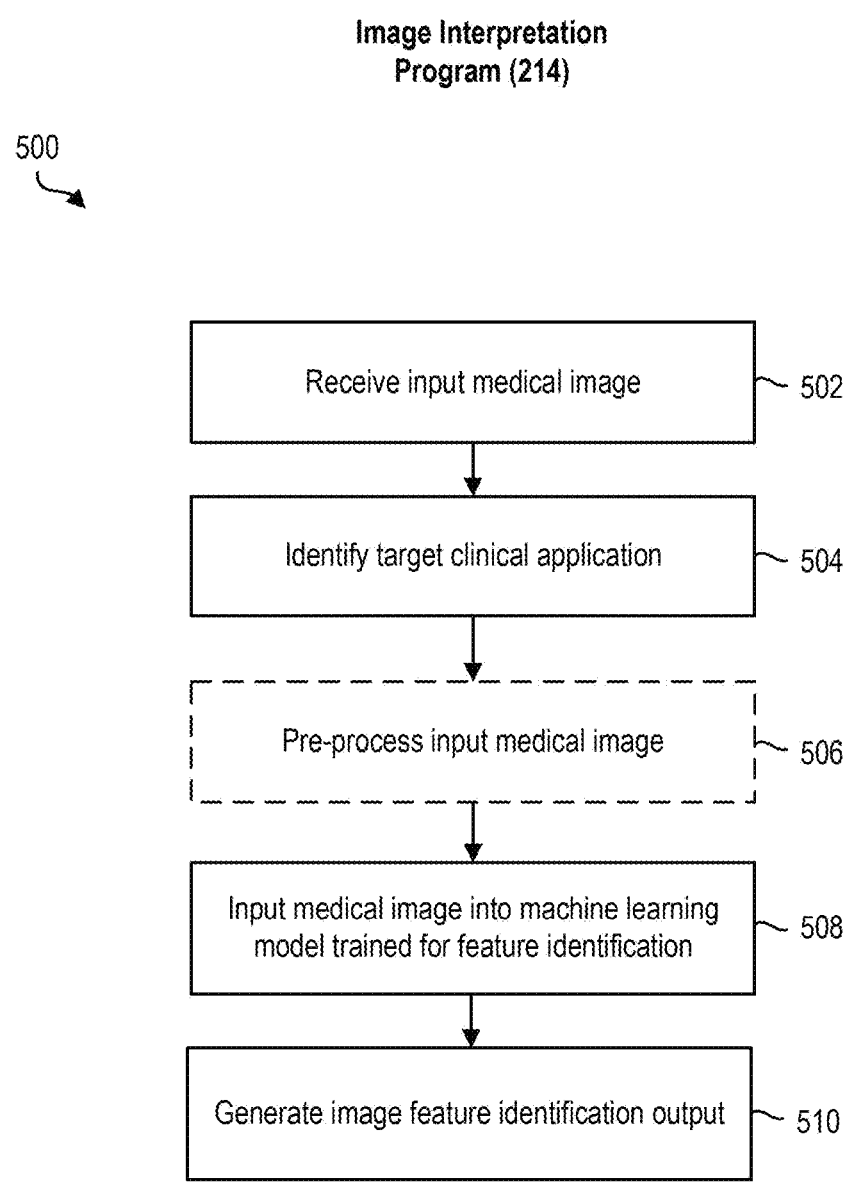
FIG. 5 is an example process flow for medical image interpretation for a target clinical application, according to some embodiments of the present invention.

Referring now to FIG. 5, there is shown a process flow for an example method 500 for analyzing one or more target features in an input image. Method 500 may be performed, for example, by the image interpretation program 214 executing on the server processor 206*a* (as shown in FIG. 2C) and/or a processor of the remote terminal 208 (as shown in FIG. 2A). For example, the method of FIG. 5 may be performed as part of act 316 in FIG. 3 or act 418 in FIG. 4 to analyze a medical image for one or more target features.

At 502, the image interpretation program 214 may receive an input image. For example, this can be an image retrieved from data storage 216 as discussed above with FIGS. 3 and 4.

At 504, the image interpretation program 214 may identify one or more target clinical applications in association with the input image. For example, a target clinical application can be identifying kidney stones, identifying kidney tumors, identifying gallstones in the gallbladder, etc. in an abdominal ultrasound image. As noted, in some cases, the target clinical applications can be identified via a user input (e.g., a user input into the remote terminal 208). In other cases, the target clinical application may be retrieved from the server 206 (e.g., if the target clinical application was inputted on the computing device 204 when executing IQ program 212).

At 506, in some embodiment, the input image can be pre-processed. This step is optional and shown in dotted outline in FIG. 5. Example pre-processing steps may include downsampling or upsampling the image, cropping the number of lengthwise or widthwise pixels of the image, scaling the image, rotating the image, processing the image through one or more noise filters, processing the image through a high contrast filter (e.g., to reduce granularity of grayscale), Sobel filters for edge detection, smoothing filters for noise reduction, and the like. Pre-processing an input image may help standardize the input image so that it matches the format (e.g., having generally the same dimensions and parameters) of the medical image the machine learning model used in step 508 is trained on. For example, the pre-processing acts performed at act 506 may be analogous to the pre-processing act 604 used in the method of FIG. 6 when normalizing training medical images. In various embodiments, performing the pre-processing acts may improve the accuracy of the prediction outputted by the machine learning model.

At 508, the input medical image along with the target clinical application can be fed into a trained machine learning model. In particular, the trained machine learning model may be configured to identify one or more target image features in association with the target clinical application. For instance, the machine learning model may be trained to segment the presence of a particular image feature (e.g., kidney stones, tumors, gallstones, etc.), and/or detect the absence of such an image feature.

A machine learning model may generally be the mathematical weights and/or parameters learned by the deep neural network during training. In some embodiments, the machine learning model used in act 508 may only be deployed if trained to satisfaction. The machine learning model may be deployed for execution on a neural network to predict image features on new input medical images. For example, the neural network may be a convolution neural network—with various nodes in the input layer, hidden layers, and output layers. However, in various embodiments, different arrangements of the neural network may be possible.

At 510, the machine learning model can generate an output (e.g., an annotated image). In some cases, the output can be displayed on a display interface (e.g., of remote terminal 208) for review (e.g., by a diagnostician, healthcare practitioner, or patient).

Figure 6:
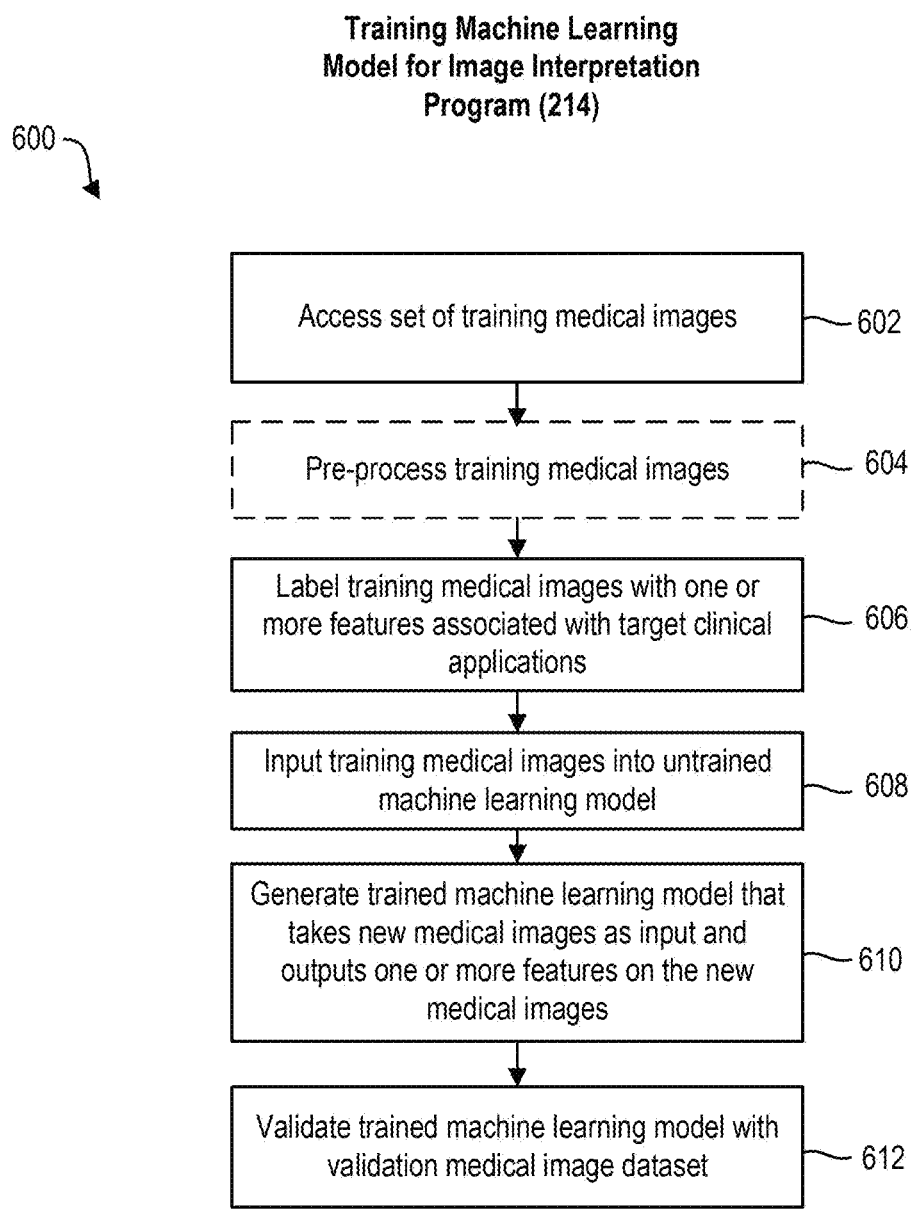
FIG. 6 is an example method for training a machine learning model to perform medical image interpretation for a target clinical application, according to some embodiments of the present invention.

Referring to FIG. 6, show there is an example process flow for a method 600 for training a machine learning model to assess features in medical images. The machine learning model that results from executing this method may be used by the image interpretation program 214 (as shown in FIG. 2C) to analyze input medical images that meet a quality value threshold (e.g., during acts 316 in FIG. 3 or 418 in FIG. 4).

At 602, a set of training medical images may be accessed. The training image data may include medical images captured in the context of various different clinical applications (e.g., kidney stones, various tumors, gallstones, etc.). In some embodiments, the method of FIG. 6 may be performed for a particular clinical application such that the set of training medical images are only related to that particular clinical application (e.g., images for identifying kidney stones).

At 604, the set of training medical images may be pre-processed. This is an optional step, and is shown in dotted outline in FIG. 6. The pre-processing acts performed in step 604 may help standardize the images for training the machine learning model, so as to improve its performance. The acts performed at step 604 may correspond to the acts discussed above with respect to act 506 in FIG. 5.

At 606, the training medical images may be labeled with one or more features associated with a target clinical application. For example, this may include identifying the feature visualized in the captured medical image (e.g., kidney stones, tumors, gallstones, etc.). In at least some embodiments, this data may be received from user input. For example, a user of the remote terminal 208 may label the features relevant for the clinical application visualized in each training image (e.g., location of kidney stones in abdominal ultrasound images).

The image labelling can be performed, for example, by a user observing the training images, via a display screen of a computing device, and manually annotating the image via a user interface. Generally, the training medical images used for a particular clinical application will only be images in which the image quality is of a sufficient quality threshold to allow for proper and accurate feature identification. For example, this can include training medical images having a quality ranging from a minimum quality in which target features are just barely visible for labelling (e.g., annotating), to excellent quality images in which the target features are easily identifiable. In various embodiments, the training medical images can have different degrees of images brightness, speckle measurement and SNR. Accordingly, the training medical images can include a graduation of training medical images ranging from images with just sufficient image quality to high image quality. In this manner, the machine learning model may be trained to identify features on training medical images that have varying levels of sufficient image quality for clinical interpretation.

At 608, the labeled training images (e.g., the original training medical image and/or pre-processed training medical image) can be inputted into an untrained machine learning model. In some embodiments, the training data can also include an indication the clinical application associated with the label used on the training medical images.

For example, the various labeled training medical images may be inputted into a deep neural network that can learn how to predict image features on new medical images. The neural network may learn to detect that certain shapes and/or locations correspond to image features relevant to certain clinical applications (e.g. kidney stones, tumors, ventricles, gallstones, etc.).

In various embodiments, the training may involve various additional acts (not shown) to generate a suitable machine learning model. For example, various deep learning techniques such as regression, classification, feature extraction, and the like may be used. Any generated machine learning model may be iteratively tested to ensure they are not overfitted and sufficiently generalized for identifying image features for intended clinical applications. In various embodiments, the machine learning may be supervised or unsupervised. For example, various types of supervised machine learning algorithms used to train the machine learning model may include Naïve-Bayes, K-Nearest Neighbor (KNN) method, support vector machines (SVM), and random forest methods.

In some embodiments, using a cross-validation method on the training process may optimize neural network hyper-parameters to try to ensure that the neural network can sufficiently learn the distribution of all possible images for a given clinical application without overfitting to the training data. In some embodiments, after finalizing the neural network architecture, the neural network may be trained on all of the data available in the training image files.

In various embodiments, batch training may be used. For example, for ultrasound images, each batch may consist of multiple images (e.g., thirty-two) where each example image may be gray-scale, 256*256 pixels, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behavior. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the model. Therefore, in some embodiments, the training images may be augmented on-the-fly while training. In every mini-batch, each sample may be translated horizontally and vertically, rotated and/or zoomed, for example.

After training has been completed, the sets of parameters stored in the storage memory may represent a trained neural network. Thus, as a result of the training of act 608, at 610, a trained machine learning model can be generated. The trained machine learning model can take new medical images as input and output one or more features on the new medical images. The trained machine learning model may represent the mathematical weights and/or parameters learned by the deep neural network to accurately predict an image feature for a target clinical application on new medical images.

In order to assess the performance of the model, the stored model parameter values can be retrieved any time to perform image assessment through applying an image to the neural networks represented thereby.

In some embodiments, the deep neural network may include various layers such as convolutional layers, max-pooling layers, and fully connected layers. In some embodiments, the final layers may include an output layer such as a softmax or sigmoid layer, which may demonstrate respective determinations that an input set of pixels fall within or not within an image feature for a particular clinical application. Accordingly, in some embodiments, the neural network may take at least one image as an input and output a binary mask indicating which pixels belong to a given feature (e.g., kidney stone, tumor, gallstone, etc.) and which do not (e.g., the AI model classifies which area each pixel belongs to).

At 612, in some cases, the trained machine learning model can be validated with a separate validation medical image dataset. For example, the validation dataset can include an independent set of images which can have varying image quality, for which the desired result of the machine learning model is known. The validation dataset may be fed into the machine learning model to assess the predictive accuracy of the machine learning model. In particular, the validation dataset can be used to determine whether, for a given target clinical application, the machine learning model is able to identify the correct relevant associated features in the image (e.g., presence of kidney stones).

Figure 7:
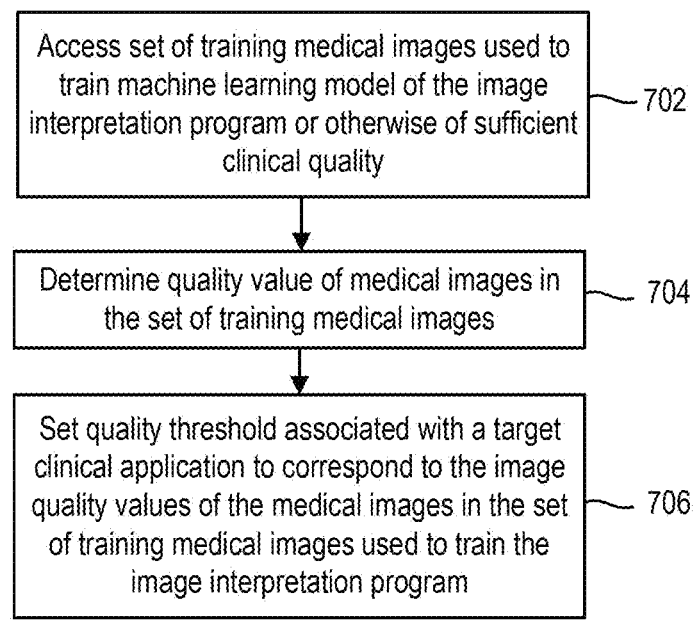
FIG. 7 is an example method for determining a quality value threshold to assess a medical image for suitability in clinical interpretation in a clinical application, according to some embodiments of the present invention.

Referring to FIG. 7, there is shown an example method 700 for determining a quality value threshold necessary to assess a medical image for suitability in clinical interpretation in a clinical application, according to some embodiments of the present invention. In particular, the method 700 can generate a quality value threshold that can be used, for example, at act 304 in FIG. 3 or act 414 in FIG. 4 discussed above.

Act 702 involves accessing a set of medical images used to train the machine learning model of the image interpretation program or are otherwise of sufficient clinical quality. The training images can include images previously captured by a medical imaging device (e.g., medical imaging device 102 of FIG. 1).

The present embodiments may generally re-use the training medical images that were used to train a machine learning model in FIG. 6. While the training performed in FIG. 6 was to generate a machine learning model that can automatically segment, classify, or otherwise identify image features with respect to a given clinical application (e.g., to identify kidney stones), it is noted that the training medical images on which the method of FIG. 6 was performed may also generally indicate the level of image quality necessary to perform clinical interpretation for that same clinical application (e.g., to identify kidney stones).

To leverage this insight, in act 704, the quality value of the images in this set of training medical images may be determined. For example, this may be performed by inputting training medical images into a machine learning model used by IQ program 212 that generates quality values or scores (e.g., 0-100% scores) as discussed above. Details for how to train the machine learning model to determine quality values for input medical images are discussed below with respect to FIG. 8.

At 706, the quality value threshold associated with a target clinical application is set to correspond to the image quality values of the medical images in the set of training images used to train the image interpretation program. For example, the quality value threshold associated with a given target clinical application may be set to the average of the quality values of the set of training medical images used in the method of FIG. 6, or the minimum quality value in the set of training medical images.

By re-using the training medical images that were used to train the feature-identification machine learning model, to also determine the quality value threshold of images necessary to perform clinical interpretation, the present embodiments make an unexpected use of such training medical images. That is, while traditional machine learning activities generally use images that are of a sufficient quality for clinical interpretation when training a feature-identification machine learning model, they generally do not consider that the feature-identification machine learning model can only be confidently deployed for real-world use if, when deployed, the future input medical images are of a sufficient quality. This is particularly true of medical imaging modalities that are operator dependent such as ultrasound imaging.

The present embodiments thus leverage the skill necessary to acquire the training medical images used for training the feature-identification machine learning model (as discussed in FIG. 6) by (i) determining a quality value associated with such images and (ii) using the quality values of such images to determine the quality value threshold necessary for new input medical images to be considered suitable for clinical interpretation. As discussed above, this may allow operators of the medical imaging device 202 (as shown in FIG. 2A—e.g., an ultrasound scanner) who are less skilled to acquire images that at suitable for clinical interpretation.

Notably, the method of FIG. 7 uses training images from the training of the clinical application-specific machine learning model to determine the quality value threshold that is necessary for a new medical image to be considered suitable for clinical interpretation. As noted, there may be different thresholds for different clinical applications because the quality of the images necessary for clinical interpretation may be different (e.g., the quality value threshold will be lower for the clinical application of identifying gallstones in the gallbladder but the quality value threshold will be higher for the clinical application of identifying kidney stones).

In various embodiments, there may be quality thresholds for various clinical applications. For example, there may be training images for different clinical applications including detection of cancerous tumors, as well as defects of the heart, abdomen, kidney, gallbladder, muscles, or other bodily organs. In some cases, the training images can also include images generated by different types of medical imaging devices (e.g., ultrasound, CT scan, etc.).

Figure 8:
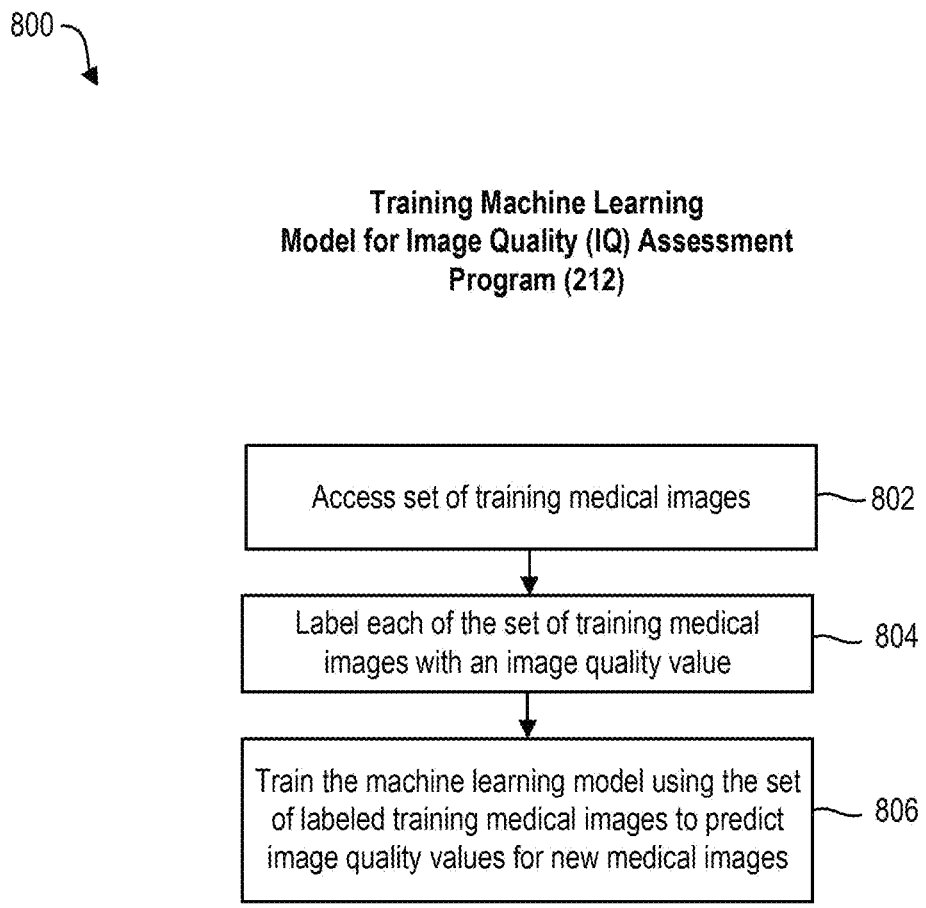
FIG. 8 is an example method for training a machine learning model to determine a quality value of a medical image, according to some embodiments of the present invention.

Referring to FIG. 8, there is shown an example method 800 for training a machine learning model to determine a quality value of a medical image. In particular, the method 800 can generate a machine learning model that can be used, for example, as part of act 304 of FIG. 3 to determine quality value of an input medical image prior to determining if the quality value meets a quality value threshold. Additionally or alternatively, the machine learning model generated from the method 800 may be used at act 404 of FIG. 4 to generate a quality value of an input medical image.

At 802, a set of training medical images may be accessed. This set of training medical images may be different from those used in FIGS. 6 and 7. As the method of FIG. 8 is to generate a machine learning model that can take as input a new medical image and output a quality value, the set of training medical images accessed at step 802 may include images having a variety of different image qualities. For example, this can include images having different degrees of images brightness, speckle measurement and SNR. Accordingly, the set of training images accessed at 802 can include a graduation of training images ranging from images with poor image quality to high image quality.

At 804, each of the set of training images may be labeled with an image quality value. For example, an expert human user may designate (e.g., input) an image quality value in relation to each training image based on their ability to delineate fine features in the image. For example, they may grade an image where they are able to discern fine features as having relatively high quality, and images where they are only able to discern coarse features as having relatively low quality. As noted, the image quality value may be stored in a variety of ways (e.g., in relatively large categorizations of 'low', 'medium', or 'high', and/or as a percentage quality indicator from 0-100%).

The image labelling can be performed, for example, by a user observing the training images, via a display screen of a computing device, and indicating a quality value for the image. As noted, the medical images used for training at act 802 includes a graduation of training images ranging from a low quality to a high quality.

At 806, the set of labeled training medical images may be used to train the machine learning model to predict image quality values on new images. The training performed at 806 may generally involve steps analogous to the steps discussed above with respect to act 608-610 of FIG. 6 when training a machine learning model to identify features for clinical applications. However, this training uses different labeled data (e.g., medical images labeled with quality values) to create a machine learning model that takes as input a new medical image and outputs a quality value of the new medical image.

As noted, the image quality value may be considered an objective measurement independent of clinical application (but in certain embodiments, may be considered modality-specific). For example, the training medical images 802 may include medical images that contain a variety of ultrasound images of varying image quality values. Some such training medical images may have a lower quality value that are suitable for one clinical application, but not another. For example, as noted above, in the case of ultrasound imaging, some training images may have a lower quality value that is only suitable for identifying gallstones in the gallbladder but not suitable for identifying kidney stones. At the same time, the training ultrasound images may also include higher quality images that are also suitable for identifying kidney stones.

Considering the methods of FIGS. 6-8 altogether, it is the quality threshold (as may be determined using the method of FIG. 7) that can link the quality value machine learning model generated using the method of FIG. 8 with the clinical application-specific image interpretation machine learning model generated using the method of FIG. 6. As shown in FIGS. 3 and 4, using the machine learning model of FIG. 8 may provide an objective quality value for a newly-inputted medical image. Then, there may be different quality thresholds for different clinical applications. And if the new image satisfies the quality threshold for a given clinical application, it may be interpreted using a machine learning model generated using the method of FIG. 6. This particular configuration enables the decoupling of skilled image acquisition from image interpretation discussed herein.

It will be appreciated that for various machine learning training acts described herein, the predictive accuracy of the model is increased and enhanced by training the model using a larger and greater array of training images.

INTERPRETATION OF TERMS

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies. In addition, as used herein, the wording "and/or" is intended to represent an inclusive or. That is, "X and/or Y" is intended to mean X or Y or both, for example. As a further example, "X, Y, and/or Z" is intended to mean X or Y or Z or any combination thereof.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The term "AI model" or "machine learning model" means a mathematical or statistical model that may be generated through artificial intelligence techniques such as machine learning and/or deep learning. For example, these techniques may involve inputting labeled or classified data into a neural network algorithm for training, so as to generate a model that can make predictions or decisions on new data without being explicitly programmed to do so. Different software tools (e.g., TensorFlow™, PyTorch™, Keras™) may be used to perform machine learning processes.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code, or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and FPGAs. Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

The invention claimed is:

1. A method for assessing medical images for suitability in clinical interpretation, the method comprising:
   acquiring a medical image of an anatomical region from a medical imaging device;
   inputting the medical image into a machine learning model that outputs quality values of medical images for the anatomical region, wherein the machine learning model is configured to determine an objective quality value of the medical image, wherein the machine learning model is trained with training images of the anatomical region, and the training images were labeled by an expert human designating an input image quality value for each training image of the training images;
   providing a first quality threshold associated with a first target clinical application for the anatomical region;
   providing a second quality threshold associated with a second target clinical application for the anatomical region, wherein the second quality threshold is lower than the first quality threshold;
   determining that the objective quality value meets the second quality threshold associated with the second target clinical application for the anatomical region, and that the objective quality value does not meet the first quality threshold associated with the first target clinical application for the anatomical region; and
   permitting clinical interpretation of the medical image for the second target clinical application for the anatomical region, and not permitting clinical interpretation of the medical image for the first target clinical application for the anatomical region.

2. The method of claim 1, wherein when it is determined that the objective quality value meets the second quality threshold associated with the second target clinical application for the anatomical region, and that the objective quality value does not meet the first quality threshold associated with the first target clinical application for the anatomical region, the method further comprises:
   analyzing the medical image to detect an image feature associated with the second target clinical application for the anatomical region.

3. The method of claim 2, wherein the method is performed on a computing device, and prior to the analyzing, the method further comprises:
   transmitting, from the computing device to a server, the medical image and the objective quality value of the machine learning model;
   storing the medical image and the quality value on the server; and
   retrieving, at the server, the medical image.

4. The method of claim 2, wherein the machine learning model is a first machine learning model, and the analyzing the medical image comprises:
   inputting the medical image into a second machine learning model, wherein the second machine learning model is configured to detect the image feature associated with the second target clinical application for the anatomical region, for medical images that meet the second quality threshold associated with the second target clinical application for the anatomical region.

5. The method of claim 4, wherein when training the second machine learning model, the method further comprises:
   accessing a set of training medical images;
   labelling, for each of the set of training medical images, the image feature associated with the second target clinical application for the anatomical region; and
   training the second machine learning model to identify the image feature on future medical images.

6. The method of claim 5, wherein to determine the second quality threshold associated with the second target clinical application for the anatomical region, the method further comprises:
   determining image quality values of the medical images in the set of training medical images; and
   setting the second quality threshold associated with the second target clinical application for the anatomical region to correspond to the image quality values of the medical images in the set of training medical images used to train the second machine learning model.

7. The method of claim 1, wherein the first target clinical application associated with the first quality threshold comprises identifying kidney stones, and the second target clinical application associated with the second quality threshold that is lower than the first quality threshold comprises identifying gallstones.

8. The method of claim 1, wherein the first target clinical application associated with the first quality threshold comprises identifying a ventricle, and the second target clinical application associated with the second quality threshold that is lower than the first quality threshold comprises identifying pericardial effusion.

9. The method of claim 1, wherein when training the machine learning model, the method further comprises:
   accessing a set of training medical images;
   labeling each of the set of training medical images with an image quality value; and
   training the machine learning model using the set of labeled training medical images to predict image quality values for new medical images.

10. A system for assessing medical images for suitability in clinical interpretation, the system comprising:
   a computing device comprising one or more device processors and a device memory storing device instructions for execution by the one or more device processors, wherein when the device instructions are executed by the one or more device processors, the one or more device processors are configured to:
      acquire a medical image of an anatomical region from a medical imaging device; and
      input the medical image into a machine learning model that outputs quality values of medical images for the anatomical region, wherein the machine learning model is configured to determine an objective quality value of the medical image, wherein the machine learning model is trained with training images of the anatomical region, and the training images were labeled by an expert human designating an input image quality value for each training image of the training images; and
   a server comprising one or more server processors and a server memory storing server instructions for execution by the one or more server processors, wherein when the server instructions are executed by the one or more server processors, the one or more server processors are configured to:
      provide a first quality threshold associated with a first target clinical application for the anatomical region;
      provide a second quality threshold associated with a second target clinical application for the anatomical region, wherein the second quality threshold is lower than the first quality threshold;
      determine that the objective quality value meets the second quality threshold associated with the second target clinical application for the anatomical region and that the objective quality value does not meet the first quality threshold associated with the first target clinical application for the anatomical region; and
      permit clinical interpretation of the medical image for the second target clinical application and not permit clinical interpretation of the medical image for the first target clinical application for the anatomical region.

11. The system of claim 10, wherein when it is determined that the objective quality value meets the second quality threshold associated with the second target clinical application for the anatomical region, and that the objective quality value does not meet the first quality threshold associated with the first target clinical application for the anatomical region, the server is further configured to:
   analyze the medical image to detect an image feature associated with the second target clinical application for the anatomical region.

12. The system of claim 11, wherein prior to the analyzing,
   the computing device is further configured to:
      transmit, to a server, the medical image and the objective quality value of the machine learning model; and
   the server is further configured to:
      store the medical image and the quality value; and
      retrieve the medical image.

13. The system of claim 11, wherein the machine learning model is a first machine learning model, and the analyzing the medical image comprises:
   inputting the medical image into a second machine learning model, wherein the second machine learning model is configured to detect the image feature associated with the second target clinical application for the anatomical region, for medical images that meet the second quality threshold associated with the second target clinical application for the anatomical region.

14. The system of claim 13, wherein when training the second machine learning model, the server is further configured to:
   access a set of training medical images;
   receive inputs that label, for each of the set of training medical images, image feature associated with the second target clinical application for the anatomical region; and
   train the second machine learning model to identify the image feature on future medical images.

15. The system of claim 14, wherein to determine the second quality threshold associated with the second target clinical application for the anatomical region, the server is further configured to:
   determine image quality values of the medical images in the set of training medical images; and
   set the second quality threshold associated with the second target clinical application for the anatomical region to correspond to the image quality values of the medical images in the set of training medical images used to train the second machine learning model.

16. The system of claim 10, wherein the first target clinical application associated with the first quality threshold comprises identifying kidney stones, and the second target clinical application associated with the second quality threshold comprises identifying gallstones.

17. The system of claim 10, wherein the first target clinical application associated with the first quality threshold comprises identifying a ventricle, and the second target clinical application associated with the second quality threshold, that is lower than the first quality threshold, comprises identifying pericardial effusion.

18. The system of claim 10, wherein when training the machine learning model, the server is further configured to:
   access a set of training medical images;
   receive inputs that label each of the set of training medical images with an image quality value; and
   train the machine learning model using the set of labeled training medical images to predict image quality values for new medical images.

* * * * *